United States Patent
Choi et al.

(10) Patent No.: US 10,390,687 B2
(45) Date of Patent: Aug. 27, 2019

(54) ENDOSCOPIC SURGICAL INSTRUMENTS

(71) Applicant: Samsung Electronics Co., Ltd., Suwon-Si, Gyeonggi-Do (KR)

(72) Inventors: Byung June Choi, Gunpo-si (KR); Yong Jae Kim, Seoul (KR); Jeong Hun Kim, Hwaseong-si (KR); Kyung Shik Roh, Seongnam-si (KR); Se Gon Roh, Suwon-si (KR); Youn Baek Lee, Suwon-si (KR); Jong Won Lee, Uiwang-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 823 days.

(21) Appl. No.: 14/202,527

(22) Filed: Mar. 10, 2014

(65) Prior Publication Data
US 2014/0257336 A1 Sep. 11, 2014

(30) Foreign Application Priority Data
Mar. 11, 2013 (KR) .................. 10-2013-0025637

(51) Int. Cl.
*A61B 1/00* (2006.01)
*A61B 1/005* (2006.01)
(Continued)

(52) U.S. Cl.
CPC .......... *A61B 1/0055* (2013.01); *A61B 1/0016* (2013.01); *A61B 1/0051* (2013.01);
(Continued)

(58) Field of Classification Search
CPC ............ A61B 1/00131; A61B 1/00147; A61B 1/00154; A61B 1/0016; A61B 1/005;
(Continued)

(56) References Cited

U.S. PATENT DOCUMENTS

2006/0199999 A1* 9/2006 Ikeda .................. A61B 1/0052
600/141
2008/0065107 A1 3/2008 Larkin et al.
(Continued)

FOREIGN PATENT DOCUMENTS

| JP | 2006-116194 A | 5/2006 |
| JP | 2008-161970 A | 7/2008 |
| KR | 2011-0132302 A | 12/2011 |

*Primary Examiner* — Ryan N Henderson
(74) *Attorney, Agent, or Firm* — Harness, Dickey & Pierce, P.L.C.

(57) ABSTRACT

An endoscopic surgical instrument may include: two surgical instrument modules, each of which is provided with a surgical instrument portion; and/or an endoscopic module configured to form a triangular shape with the two surgical instrument modules and configured to capture operations of the surgical instrument modules at different angles using a plurality of joints. Wires connecting respective members coupled by the plurality of joints may be configured to amplify drive forces of a drive portion applied to the plurality of joints. The plurality of joints may include rolling joints at which teeth of gears engage and rotate with each other. The plurality of joints may provide three or more degrees of freedom to the endoscopic module.

12 Claims, 12 Drawing Sheets

(51) Int. Cl.
    *A61B 17/29*     (2006.01)
    *A61B 34/00*     (2016.01)
    *A61B 34/30*     (2016.01)
    *A61B 34/35*     (2016.01)
    *A61B 90/00*     (2016.01)

(52) U.S. Cl.
    CPC .......... *A61B 1/00147* (2013.01); *A61B 34/30* (2016.02); *A61B 34/35* (2016.02); *A61B 34/70* (2016.02); *A61B 34/71* (2016.02); *A61B 90/361* (2016.02); *A61B 2017/2906* (2013.01); *A61B 2017/2908* (2013.01); *A61B 2034/305* (2016.02); *A61B 2034/306* (2016.02)

(58) Field of Classification Search
    CPC ... A61B 1/0051; A61B 1/0052; A61B 1/0053; A61B 1/0055; A61B 1/0056; A61B 1/0057; A61B 1/0058; A61B 1/008; A61B 34/30; A61B 34/32; A61B 34/35; A61B 34/37; A61B 34/70–72; A61B 2034/301–306
    USPC ........ 600/104, 106, 107, 114, 115, 127–130, 600/121–125, 139–152; 604/528; 606/1, 606/130
    See application file for complete search history.

(56) References Cited

U.S. PATENT DOCUMENTS

| | | |
|---|---|---|
| 2011/0230894 A1 | 9/2011 | Simaan et al. |
| 2014/0142377 A1* | 5/2014 | Yang .................... A61B 1/0055 600/104 |

* cited by examiner

ENDOSCOPIC SURGICAL INSTRUMENTS

CROSS-REFERENCE TO RELATED APPLICATION(S)

This application claims priority from Korean Patent Application No. 10-2013-0025637, filed on Mar. 11, 2013, in the Korean Intellectual Property Office (KIPO), the entire contents of which are incorporated herein by reference.

BACKGROUND

1. Field

Some example embodiments may relate to endoscopic surgical instruments configured to allow an incision part to be minimized and/or configured to allow a precise image for a part to be operated to be obtained by tilting an endoscopic module having various joints in order to secure a clear view within the human body during operation.

2. Description of Related Art

In general, existing open abdominal surgery to treat a patient may involve making an incision in the skin to reach a surgical target. Open abdominal surgery may secure a clear view, but may entail long recovery time and/or may cause scarring after operation due to a large incision and/or a large amount of bleeding during the operation. Thus, to overcome such defects associated with open abdominal surgery, laparoscopic surgery has been developed. Laparoscopic surgery may involve forming a plurality of small apertures through the skin, and then inserting an endoscope and various surgical instruments into the human body through the apertures. This laparoscopic surgery may have advantages compared to the open abdominal surgery in that scarring may be minimized and/or patient recovery time may be dramatically reduced after the operation.

Recently, single port laparoscopic surgery has been developed in which a surgical instrument and/or an endoscope may be inserted into the human body through one aperture present in a part such as a navel or the like. Single port laparoscopic surgery may have advantages in that an incision part required for a procedure may be small, an amount of bleeding during the procedure may be notably less compared to the open abdominal surgery, patient recovery period may be fast, and/or scarring may be minimized or may hardly exists after the operation. Therefore, single port laparoscopic surgery has become increasingly popular.

When single port laparoscopic surgery is performed, a specifically designed endoscopic device may be used to secure a clear view for a part to be operated through a minimal incision in the human body. The endoscopic device may be a medical image device for the single port laparoscopic surgery in which a clear view for the inside of the patient's body may not be directly secured. Accordingly, in the single port laparoscopic surgery, an operator may perform surgery while viewing an image for a part to be operated through the endoscopic device.

SUMMARY

In some example embodiments, an endoscopic surgical instrument may comprise: two surgical instrument modules, each of which is provided with a surgical instrument portion; and/or an endoscopic module configured to form a triangular shape with the two surgical instrument modules and configured to capture operations of the surgical instrument modules at different angles using a plurality of joints. Wires connecting respective members coupled by the plurality of joints may be configured to amplify drive forces of a drive portion applied to the plurality of joints. The plurality of joints may comprise rolling joints at which teeth of gears engage and rotate with each other. The plurality of joints may provide three or more degrees of freedom to the endoscopic module.

In some example embodiments, the endoscopic module may comprise: a head portion including a camera; and/or an arm portion connected to the head portion. The arm portion may be connected to the drive portion through a connection portion.

In some example embodiments, the head portion may comprise: a first gear portion including first teeth; and/or a second gear portion including second teeth at a first side thereof. When the head portion rotates in left and right directions, the first teeth and the second teeth may engage and rotate with each other.

In some example embodiments, the first and second gear portions may be provided with wire mounting portions. Wires connected to the drive portion may be wound around the wire mounting portions of the first and second gear portions.

In some example embodiments, the wire mounting portions of the first and second gear portions may comprise: first wire mounting portions provided at left sides of the first and second gear portions; and/or second wire mounting portions provided at right sides of the first and second gear portions.

In some example embodiments, a first wire may be wound around the first wire mounting portions. A second wire may be wound around the second wire mounting portions. When one of the first and second wires is contracted by the drive portion and the other one of the first and second wires extends, the head portion may be configured to rotate toward the contracted one of the first and second wires.

In some example embodiments, the second gear portion may include third teeth at a second side thereof. A direction in which the second teeth extend on the first side of the second gear portion may form a right angle with a direction in which the third teeth extend on the second side of the second gear portion.

In some example embodiments, the arm portion may comprise a third gear portion. A first side of the third gear portion may include fourth teeth corresponding to the third teeth.

In some example embodiments, when the head portion is tilted in upward and downward directions, the third teeth and the fourth teeth may engage and rotate with each other.

In some example embodiments, the second side of the second gear portion and the first side of the third gear portion may be provided with wire mounting portions. Wires connected to the drive portion may be wound around the wire mounting portions of the second side of the second gear portion and the first side of the third gear portion.

In some example embodiments, the wire mounting portions of the second side of the second gear portion and the first side of the third gear portion may comprise: third wire mounting portions respectively provided at upper portions of the second and third gear portions; and/or fourth wire mounting portions respectively provided at lower portions of the second and third gear portions.

In some example embodiments, a third wire may be wound around the third wire mounting portions. A fourth wire may be wound around the fourth wire mounting portions. When one of the third and fourth wires is contracted by the drive portion and the other one of the third and fourth wires extends, the head portion may be configured to rotate and tilt toward the contracted one of the third and fourth wires.

In some example embodiments, a second side of the third gear portion may include fifth teeth. The connection portion may include sixth teeth corresponding to the fifth teeth. When the arm portion is tilted in upward and downward directions, the fifth teeth and the sixth teeth may engage and rotate with each other.

In some example embodiments, an upper side of the third gear portion and a lower side of the connection portion may be respectively provided with wire mounting portions. Fifth and sixth wires connected to the drive portion may be wound around the respective wire mounting portions of the upper side of the third gear portion and the lower side of the connection portion. When one of the fifth and sixth wires is contracted by the drive portion and the other one of the fifth and sixth wires extends, the arm portion may be configured to rotate and tilt toward the contracted one of the fifth and sixth wires.

In some example embodiments, a tilting direction or a tilting angle of the head portion or the arm portion may be configured to vary according to a direction or a length in which the second teeth, the third teeth, the fourth teeth, the fifth teeth, or the sixth teeth extend.

In some example embodiments, an endoscopic surgical instrument may comprise: a surgical instrument module configured to insert into a human body to perform an operation; and/or an endoscopic module having a plurality of joints and configured to tilt by contract or extension of wires that are provided at the plurality of joints and are connected to a drive portion. The endoscopic module may comprise a head portion including a camera, and an arm portion tiltably connected with a connection portion connected to the head and drive portions. The wires may be wound several turns around respective members formed with the plurality of joints so that drive forces of the drive portion are amplified and transferred to the plurality of joints.

In some example embodiments, the head portion may comprise: a first gear portion; and/or a second gear portion connected to the first gear portion by a link. When the head portion rotates in a left or right direction, first teeth formed on the first gear portion and second teeth formed on a first side of the second gear portion may engage and rotate with each other.

In some example embodiments, a second side of the second gear portion may be formed with third teeth. A first side of the arm portion may be formed with fourth teeth engaging with the third teeth formed on the second gear portion. When the head portion is tilted relative to the arm portion in upward and downward directions, the third teeth and the fourth teeth may engage and rotate with each other.

In some example embodiments, the connection portion may be formed with sixth teeth. The other side of the arm portion may be formed with teeth engaging with the sixth teeth of the connection portion. When the arm portion is tilted relative to the connection portion, the sixth teeth and the fifth teeth may engage and rotate with each other.

In some example embodiments, the endoscopic surgical instrument may further comprise: a second surgical instrument module. The endoscopic module may be configured to form a triangular shape with the surgical instrument modules and/or may be configured to tilt in left and right directions or upward and downward directions, thereby enabling operations of the surgical instrument modules to be captured by the endoscopic module at several positions.

In some example embodiments, an endoscopic surgical instrument may comprise: a first surgical instrument module including a first surgical instrument portion; a second surgical instrument module including a second surgical instrument portion; and/or an endoscopic module configured to capture operations of the first surgical instrument module, the second surgical instrument module, or the first and second surgical instrument modules at different angles using a plurality of joints. The endoscopic module may comprise first, second, and third members. The first and second members may be coupled by a first joint including teeth that engage and rotate with each other. The second and third members may be coupled by a second joint including teeth that engage and rotate with each other. The third member may be coupled to a connection portion by a third joint including teeth that engage and rotate with each other. The first, second, and third joints may provide three or more degrees of freedom to the endoscopic module.

In some example embodiments, wires acting at the first joint may be configured to amplify drive forces of a drive portion applied to first joint via the wires.

In some example embodiments, wires acting at the second joint may be configured to amplify drive forces of a drive portion applied to second joint via the wires.

In some example embodiments, wires acting at the third joint may be configured to amplify drive forces of a drive portion applied to third joint via the wires.

In some example embodiments, the endoscopic module may comprise a camera.

In some example embodiments, the endoscopic module may be configured to provide images from an inside of a body during surgery.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
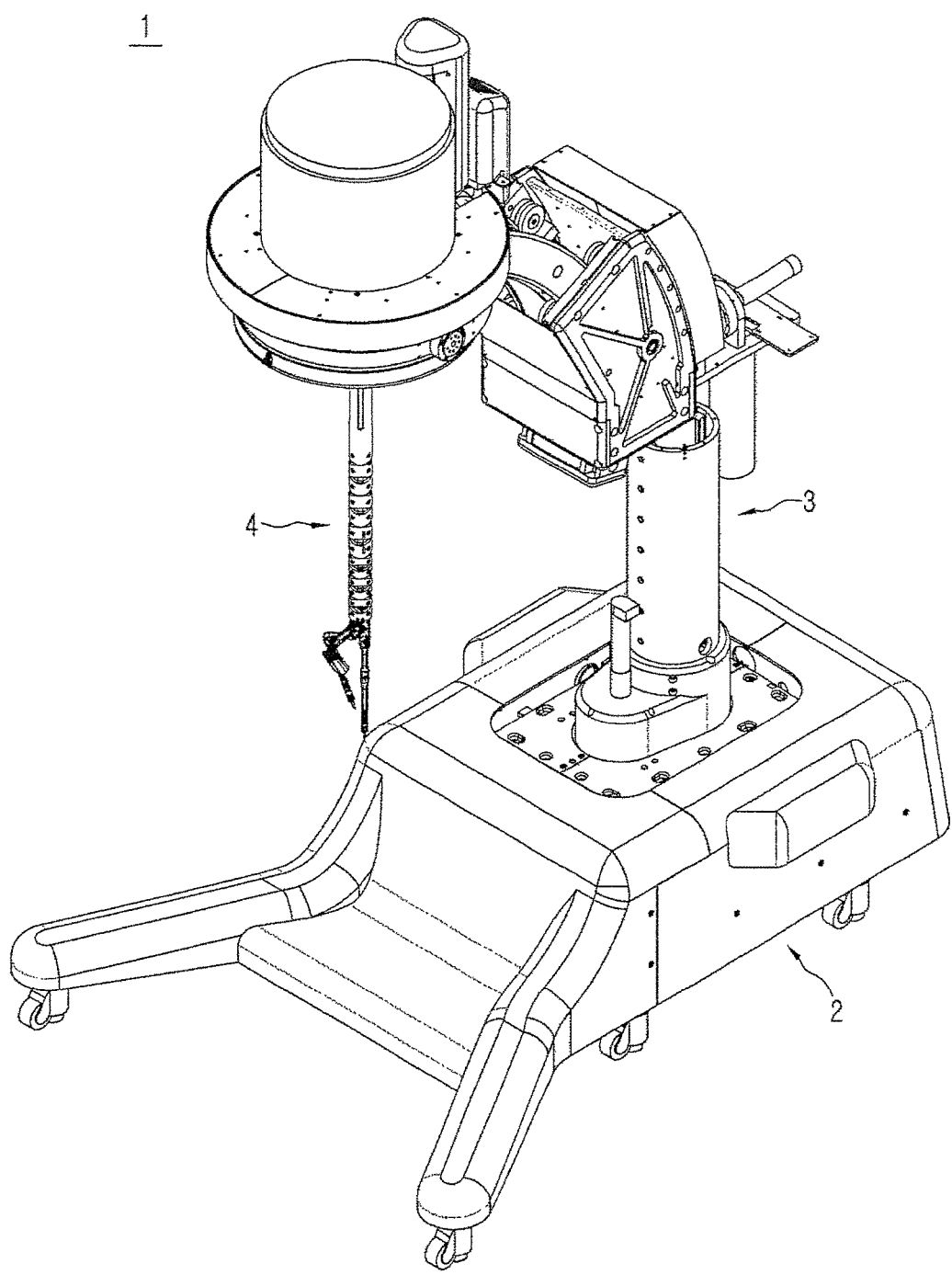
FIG. 1 is a view illustrating a surgical robot according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 2:
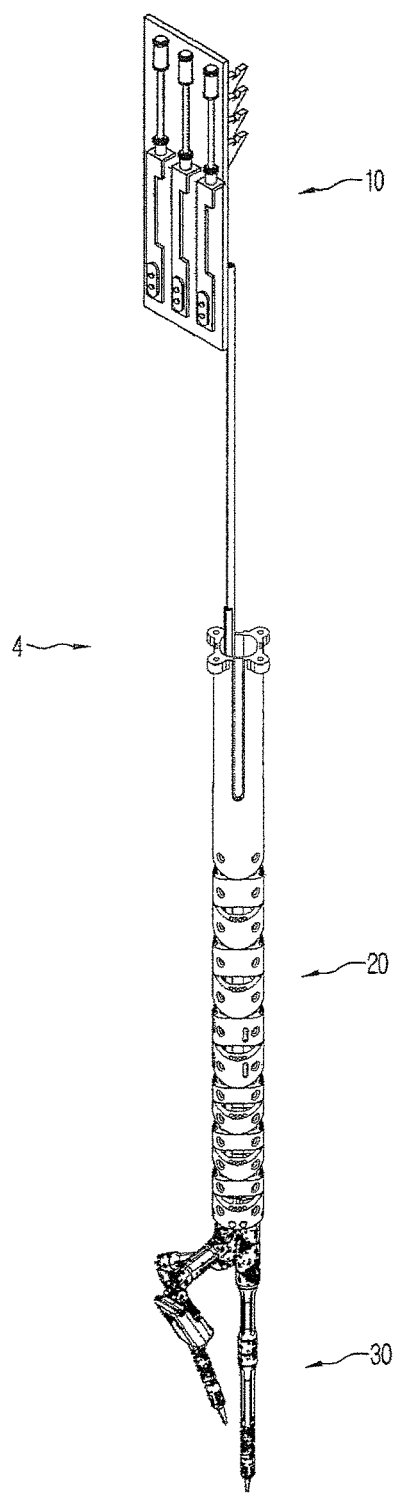
FIG. 2 is a view illustrating an endoscopic surgical unit according to some example embodiments.

FIG. 1 is a view illustrating a surgical robot according to some example embodiments. FIG. 2 is a view illustrating an endoscopic surgical unit according to some example embodiments.

Referring to FIGS. 1 and 2, a surgical robot 1 according to some example embodiments includes a base 2, a support portion 3, and an endoscopic surgical unit 4. The base 2 supports the support portion 3, and the endoscopic surgical unit 4 is mounted to the support portion 3. The endoscopic surgical unit 4 is mounted to the support portion 3 to be spaced apart from the bottom surface by a certain distance, thereby enabling a medical procedure to be easily performed upon a patient lying on an operating table.

The endoscopic surgical unit 4 includes a drive portion 10, a connection portion 20, and an endoscopic surgical instrument 30. The drive portion 10 may be mounted to the support portion 3. The endoscopic surgical instrument 30 may be inserted into the human body to perform a medical procedure. The connection portion 20 connects the endoscopic surgical instrument 30 to the drive portion 10. The endoscopic surgical instrument 30 may be operated by receiving drive force through the connection portion 20 from the drive portion 10.

Hereinafter, the endoscopic surgical instrument according to some example embodiments will be described in detail with reference to the drawings.

Figure 3:
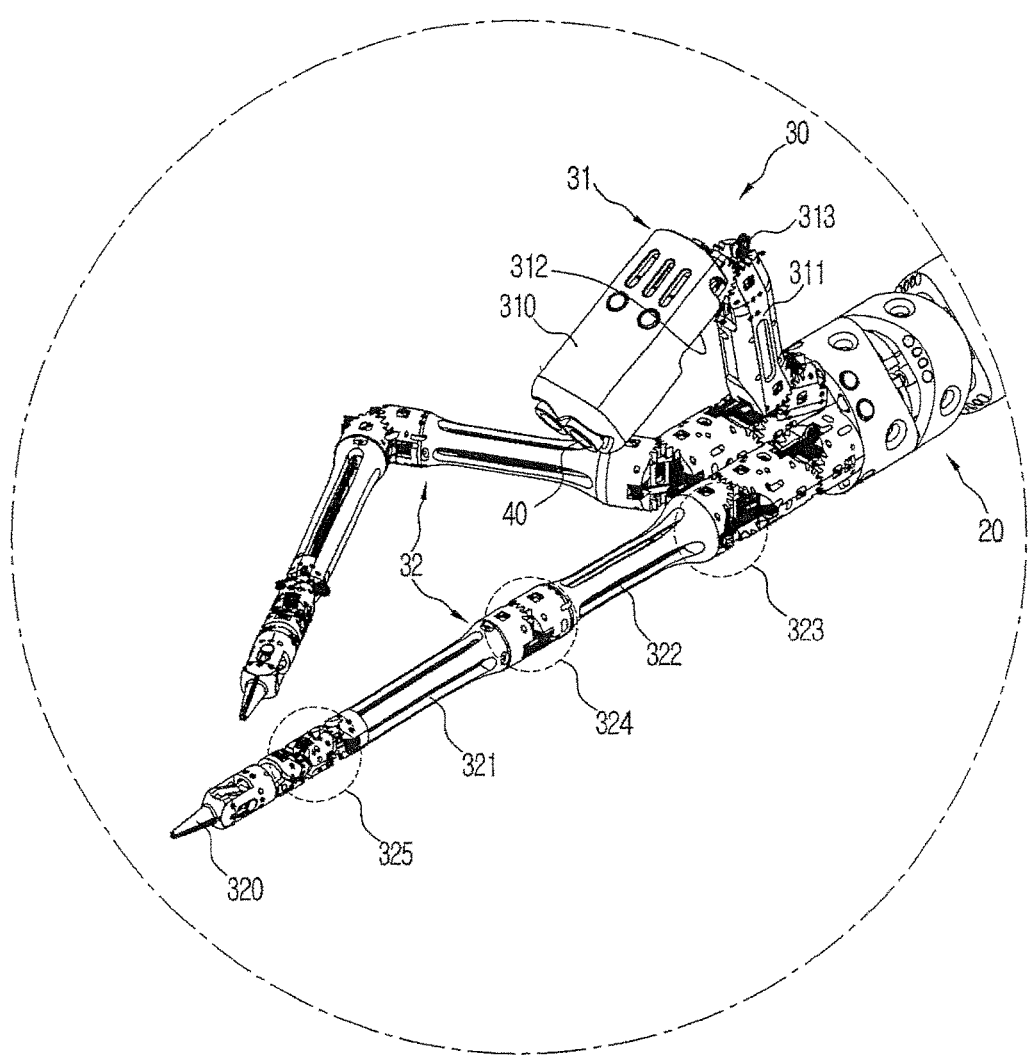
FIG. 3 is a view illustrating an endoscopic surgical instrument according to some example embodiments.

FIG. 3 is a view illustrating a portion of the endoscopic surgical instrument according to some example embodiments.

Referring to FIG. 3, the endoscopic surgical instrument 30 according to some example embodiments includes an endoscopic module 31 and a surgical instrument module 32. The endoscopic surgical instrument 30 may be provided at one end portion of the connection portion 20 to be inserted into the human body during an operation. Two surgical instrument modules 32 may be provided.

An end portion of the endoscopic module 31 and end portions of the two surgical instrument modules 32 may be located at positions corresponding to the apexes of a triangle, respectively. That is, the two surgical instrument modules 32 and the endoscopic module 31 may form a triangular shape. For example, when the endoscopic module 31 is located above and the two surgical instrument modules 32 are located below, a camera 40 provided in the endoscopic module 31 may capture operation states of the two instrument modules 32 while a user views the operation states.

The endoscopic module 31 includes a head portion 310 to which the camera 40 is mounted and an arm portion 311. The head portion 310 may be provided with a first joint 312 by which the endoscopic module 31 is bent such that the camera 40 may capture another position. The head portion 310 and the arm portion 311 may be bendably connected to each other by a second joint 313. The head portion 310 is operated by the second joint 313 so that a camera's view may be adjusted. For example, the first joint 312 may be provided such that the head portion 310 may be tilted in both left and right directions, and the second joint 313 may be provided such that the head portion 310 may be tilted in upward and downward directions. A detailed configuration of the endoscopic module 31 will be described below.

The endoscopic module 31 and each surgical instrument module 32 may have joints. The endoscopic module 31 and the surgical instrument module 32 may operate in order to easily perform an operation by being bent about the joints. For example, the surgical instrument module 32 may include a first arm 321, a second arm 322, and a surgical instrument portion 320. A first joint portion 325 may be provided between the first arm 321 and the surgical instrument portion 320, and a second joint portion 324 may be provided between the first arm 321 and the second arm 322. The first arm 321 and the surgical instrument portion 320 may be bent about the first joint portion 325.

In more detail, an end portion of the first arm 321 is formed with a toothed gear portion, and one end portion of the surgical instrument portion 320 is formed with a toothed gear portion corresponding to the gear portion formed at the first arm 321. Consequently, the gear portion formed at the first arm 321 and the gear portion formed at the surgical instrument portion 320 engage and rotate with each other, thereby enabling the first arm 321 or the surgical instrument portion 320 to be bent. Similarly to the first arm 321 and the surgical instrument portion 320, the first arm 321 and the second arm 322 may be bent about the second joint portion 324. The second arm 322 may be connected to the connection portion 20 by a third joint portion 323. Similarly to the first arm 321 and the surgical instrument portion 320, the second arm 322 may be bent by rotation of a gear portion provided at the third joint portion 323.

Figure 4:
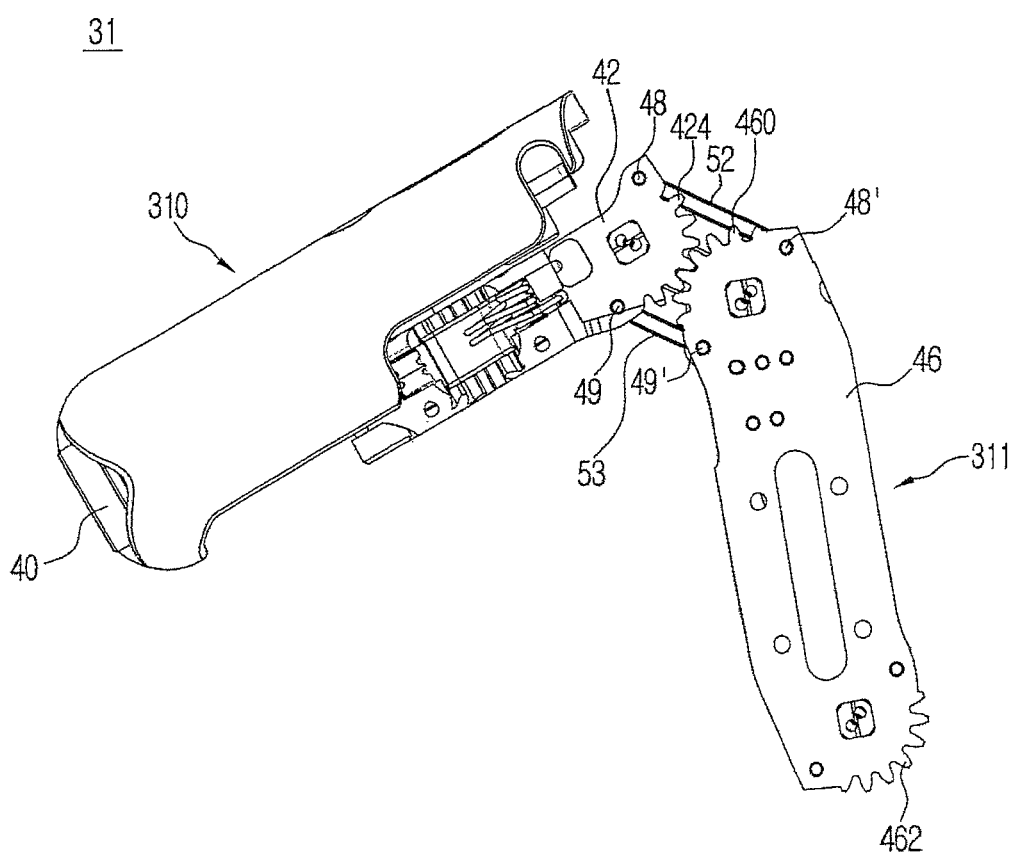
FIG. 4 is a view illustrating a detailed structure of an endoscopic module according to some example embodiments.
Figure 5:
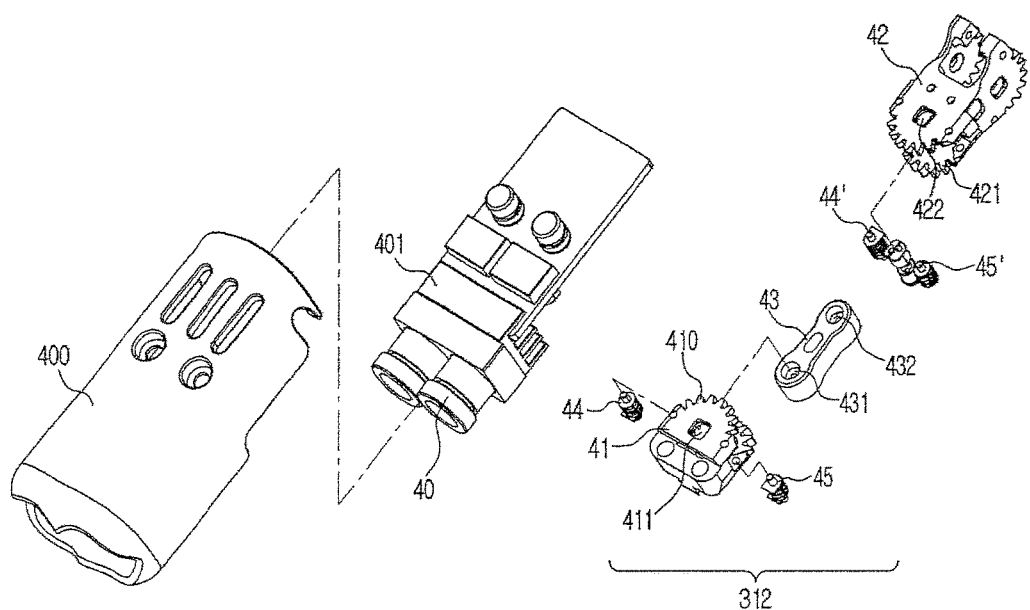
FIG. 5 is an exploded perspective view illustrating a first joint of the endoscopic module according to some example embodiments.
Figure 6:
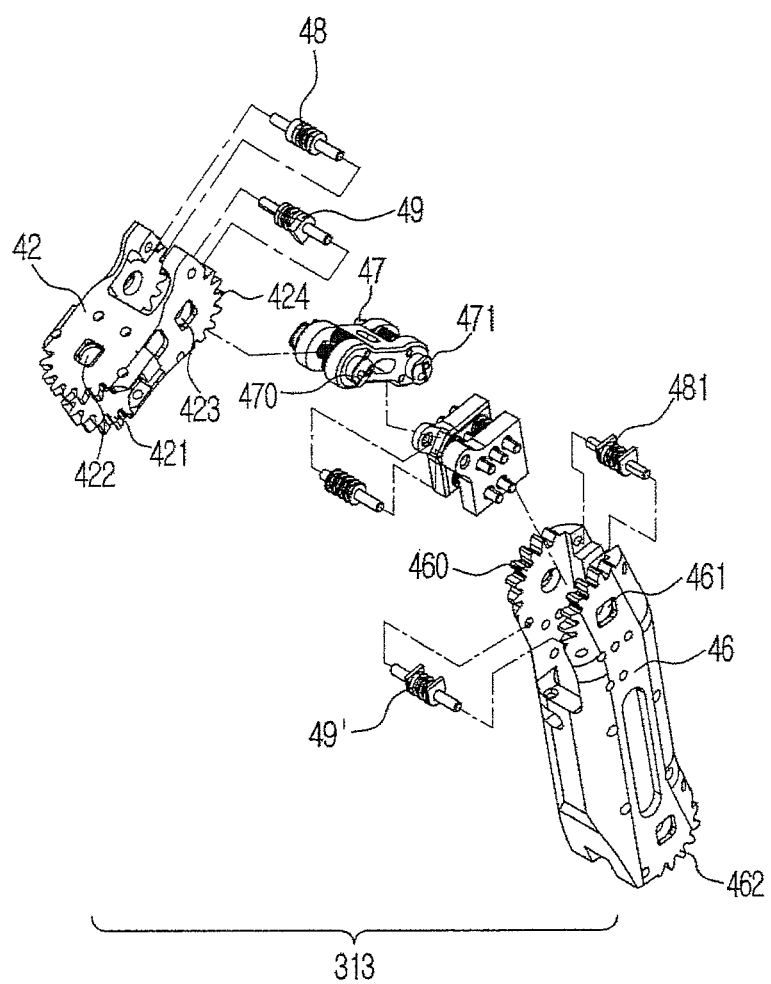
FIG. 6 is an exploded perspective view illustrating a second joint of the endoscopic module according to some example embodiments.
Figure 7:
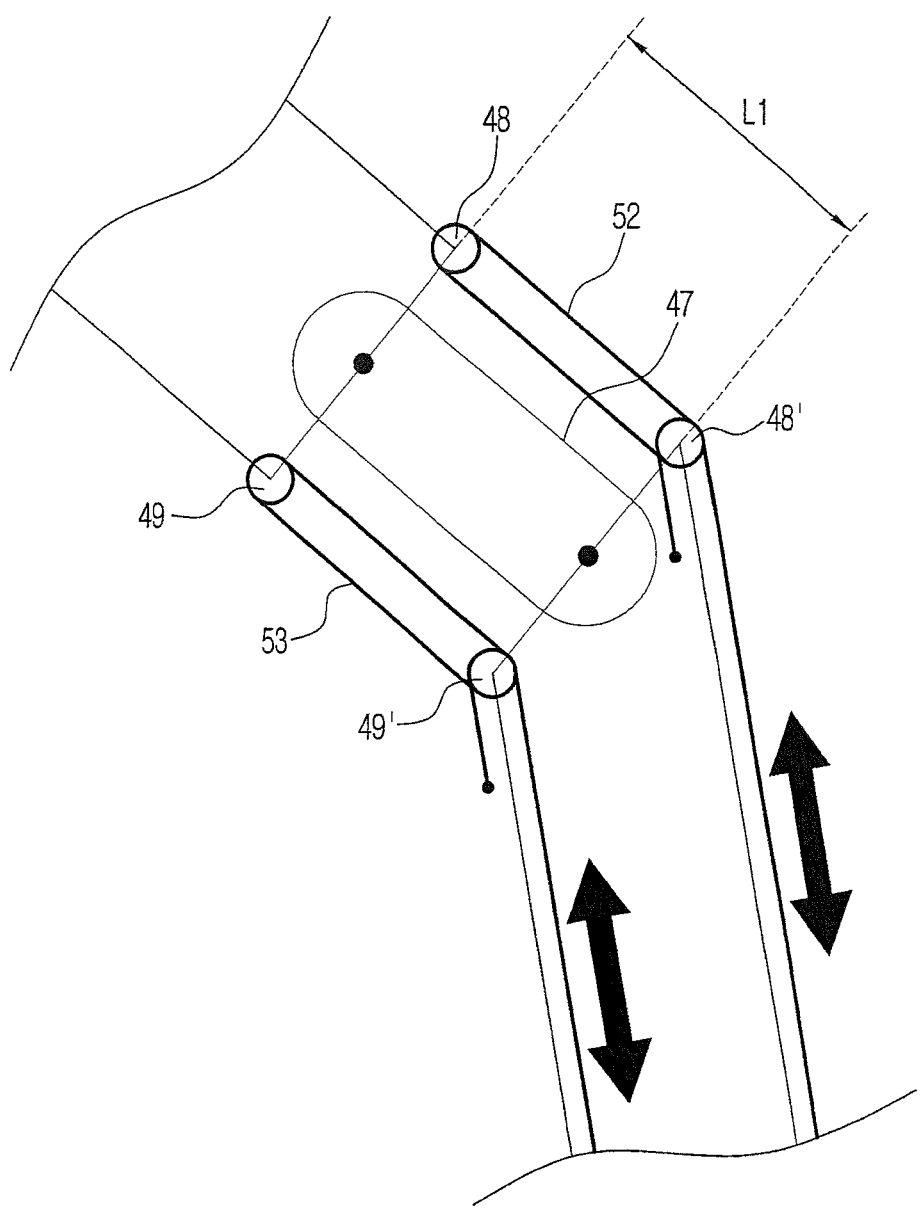
FIGS. 7 and 8 are views schematically illustrating the structure of the endoscopic module according to some example embodiments.
Figure 8:
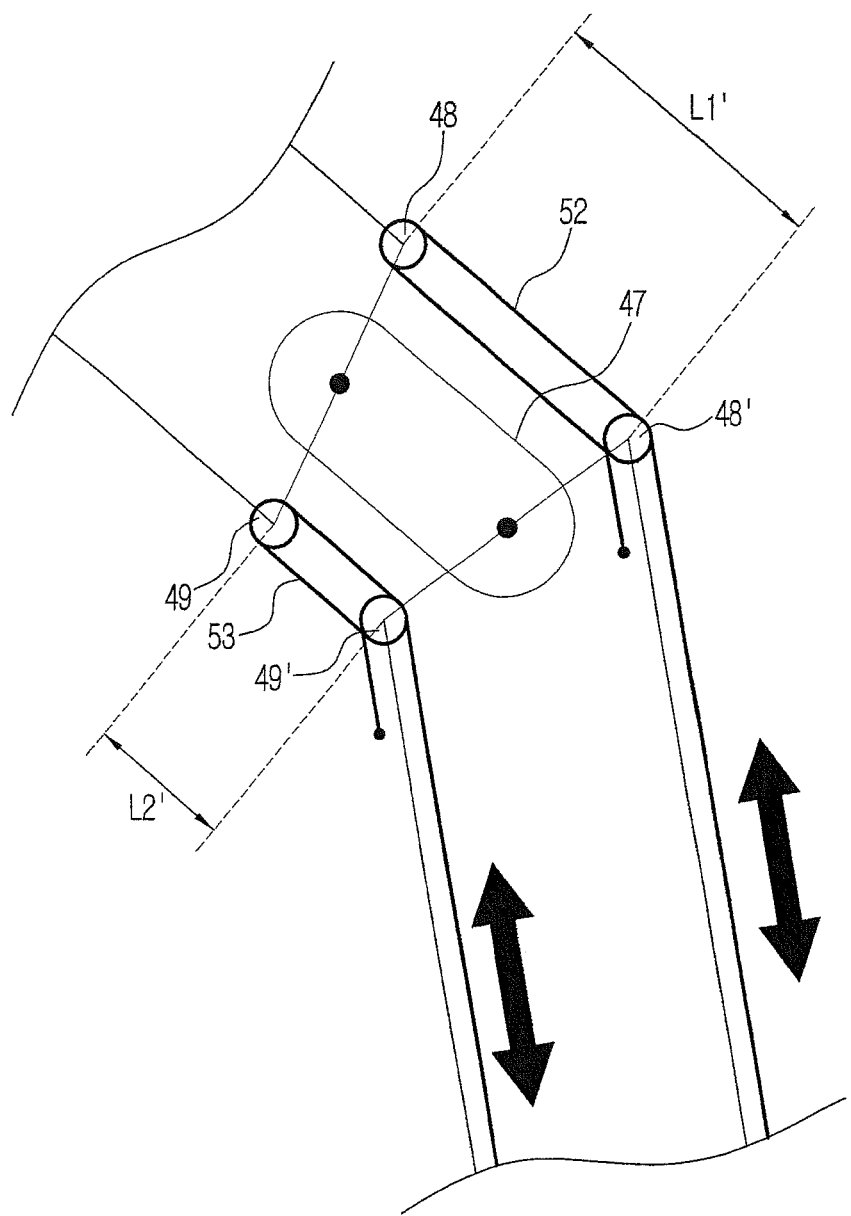

FIG. 4 is a view illustrating a detailed structure of the endoscopic module according to some example embodiments. FIG. 5 is an exploded perspective view illustrating a first joint of the endoscopic module according to some example embodiments. FIG. 6 is an exploded perspective view illustrating a second joint of the endoscopic module according to some example embodiments. FIGS. 7 and 8 are views schematically illustrating the structure of the endoscopic module according to some example embodiments.

Referring to FIGS. 4 to 8, the endoscopic module 31 according to some example embodiments includes the head portion 310 and the arm portion 311. The head portion 310 may be connected to one side of the arm portion 311 and the other side of the arm portion 311 may be connected to the connection portion 20. The head portion 310 is provided a first joint 312 so as to be tiltable in both left and right directions. The head portion 310 and the arm portion 311 may be tiltably connected to each other such that the head portion 310 may move in upward and downward directions by a second joint 313. The arm portion 311 and the connection portion 20 may be tiltably connected to each other such that the arm portion 311 may move in upward and downward directions by a third joint 314.

The head portion 310 includes a camera 40, a circuit portion 401 connected to the camera 40, and a case 400 covering the circuit portion 401. The camera 40 may be mounted to the front of the case 400. The circuit portion 401 may be connected to a first gear portion 41 constituting the first joint 312. By connecting the circuit portion 401 to the first gear portion 41, the circuit portion 401, the case 400, and the camera 40 may rotate together with the first gear portion 41.

The head portion 310 may be connected to the arm portion 311 by the first joint 312. The first joint 312 includes the first gear portion 41, a second gear portion 42, and a first link 43. The first and second gear portions 41 and 42 may be connected to each other by the first link 43.

Referring to FIG. 6, one side of the first gear portion 41 may be formed with a plurality of first teeth 410. One side of the second gear portion 42 may be formed with a plurality of second teeth 421 corresponding to the first teeth 410 of the first gear portion 41. The first teeth 410 of the first gear portion 41 and the second teeth 421 of the second gear portion 42 may be configured to engage and rotate with each other.

The first gear portion 41 may be formed with a first fastening hole 411. The second gear portion 42 may be formed with a second fastening hole 422. The first link 43 may be formed with a third fastening hole 431 and a fourth fastening hole 432. The first gear portion 41 and the first link 43 may be coupled to each other by a fastening member passing through the first fastening hole 411 and the third fastening hole 431, and the second gear portion 42 and the first link 43 may be coupled to each other by a fastening member passing through the second fastening hole 422 and the fourth fastening hole 432. In this case, the first and second gear portions 41 and 42 may be coupled to the first link 43 such that the first teeth 410 of the first gear portion 41 and the second teeth 421 of the second gear portion 42 may engage and rotate with each other.

The first and second gear portions 41 and 42 may be provided with first wire mounting portions 44 and 44', respectively. A first wire 50 may be wound around the first wire mounting portions 44 and 44'. The first wire 50 wound around the first wire mounting portions 44 and 44' may be connected through the connection portion 20 to a motor (not shown) provided in the drive portion 10. The first wire 50 may extend or contract by rotation of the motor (not shown) provided in the drive portion 10.

The first and second gear portions 41 and 42 may be further provided with second wire mounting portions 45 and 45', respectively. For example, when the first wire mounting portions 44 and 44' are provided at left sides of the first and second gear portions 41 and 42, the second wire mounting portions 45 and 45' may be provided at right sides of the first and second gear portions 41 and 42. A second wire 51 may be wound around the second wire mounting portions 45 and 45'. The second wire 51 wound around the second wire mounting portions 45 and 45' may be connected through the connection portion 20 to the motor (not shown) provided in the drive portion 10. The second wire 51 may extend or contract by rotation of the motor (not shown) provided in the drive portion 10.

The second wire 51 may contract when the first wire 50 extends by rotation of the motor of the drive portion 10, and the second wire 51 may extend when the first wire 50 contracts. The first teeth 410 of the first gear portion 41 and the second teeth 421 of the second gear portion 42 may engage and rotate with each other by extension or contraction of the first and second wires 50 and 51. Consequently, the head portion 310 may rotate in left and right directions.

For example, when the first wire 50 extends and the second wire 51 contracts, the head portion 310 may rotate in a direction toward the right side at which the contracted second wire 51 is located. When the first wire 50 contracts and the second wire 51 extends, the head portion 310 may rotate in a direction toward the left side at which the contracted first wire 50 is located.

Meanwhile, the first wire 50 may serve as a reducer by being wound several turns around the first wire mounting portions 44 and 44'. Similarly, the second wire 51 may serve as a reducer by being wound several turns around the second wire mounting portions 45 and 45'. For example, when the first wire 50 is wound several turns around the first wire mounting portions 44 and 44', drive force of the drive portion may be amplified and transferred to the first joint 312. In addition, drive force of the drive portion may be amplified by the second wire 51 which is wound several turns around the second wire mounting portions 45 and 45' and be transferred to the first joint 312.

Figure 9:
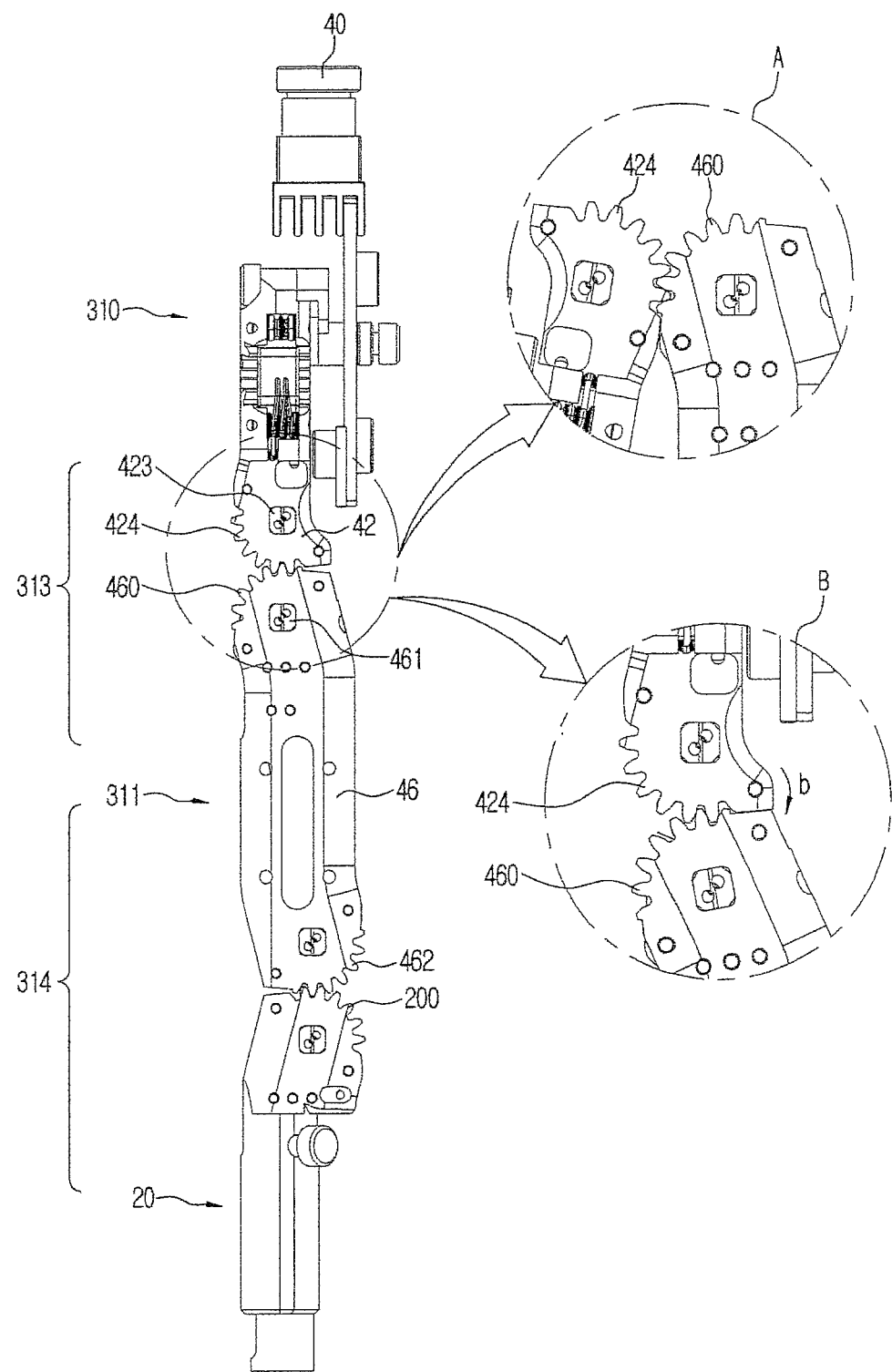
FIGS. 9 and 10 are views illustrating a tilted state of the endoscopic module according to some example embodiments.

Referring to FIG. 9, the other side of the second gear portion 42 may be formed with third teeth 424. A third gear portion 46 constituting the arm portion 311 may be formed with fourth teeth 460 corresponding to the third teeth 424 formed on the other side of the second gear portion 42. A direction in which a portion formed with the second teeth 421 on one side of the second gear portion 42 extends may form, for example, a right angle with a direction in which a portion formed with the third teeth 424 on the other side of the second gear portion 42 extends. As an example, when the second teeth 421 formed on one side of the second gear portion 42 engage and rotate with the first teeth 410 of the first gear portion 41, the head portion 310 may rotate in the left and right directions. When the third teeth 424 formed on the other side of the second gear portion 42 engage and rotate with the fourth teeth 460 of the third gear portion 46 constituting the arm portion 311, the head portion 310 may rotate in the upward and downward directions.

The other side of the second gear portion 42 may be formed with a fifth fastening hole 423. The third gear portion 46 may be formed with a sixth fastening hole 461. A second link 47 may be formed with a first rotary shaft 470 capable of being inserted into the fifth fastening hole 423 formed at the second gear portion 42 and a second rotary shaft 471 capable of being inserted into the sixth fastening hole 461 formed at the third gear portion 46. The first rotary shaft 470 formed at the second link 47 may be inserted into the fifth fastening hole 423 of the second gear portion 42, and the second rotary shaft 471 may be inserted into the sixth fastening hole 461 of the third gear portion 46. Consequently, the second gear portion 42 and the third gear portion 46 may be connected to each other by the second link 47. In this case, the third teeth 424 of the second gear portion 42 and the fourth teeth 460 of the third gear portion 46 may be configured to engage and rotate with each other.

The second and third gear portions 42 and 46 may be provided with third wire mounting portions 48 and 48', respectively. A third wire 52 may be wound around the third wire mounting portions 48 and 48'. The third wire 52 wound around the third wire mounting portions 48 and 48' may be connected through the connection portion 20 to the motor (not shown) provided in the drive portion 10. The third wire 52 may extend or contract by rotation of the motor (not shown) provided in the drive portion 10.

The second and third gear portions 42 and 46 may be further provided with fourth wire mounting portions 49 and 49', respectively. The third wire mounting portions 48 and 48' and the fourth wire mounting portions 49 and 49' may be disposed in the upward and downward directions. For example, when the third wire mounting portions 48 and 48' are respectively mounted to upper sides of the second and third gear portions 42 and 46, the fourth wire mounting portions 49 and 49' may be respectively mounted to lower sides of the second and third gear portions 42 and 46. A fourth wire 53 may be wound around the fourth wire mounting portions 49 and 49'. The fourth wire 53 wound around the fourth wire mounting portions 49 and 49' may be connected through the connection portion 20 to the motor (not shown) provided in the drive portion 10. The fourth wire 53 may extend or contract by rotation of the motor (not shown) provided in the drive portion 10.

The fourth wire 53 may contract when the motor of the drive portion 10 rotates and the third wire 52 extends, and the fourth wire 53 may extend when the third wire 52 contracts. The third teeth 424 of the second portion 42 and the fourth teeth 460 of the third gear portion 46 may engage and rotate with each other by extension or contraction of the third and fourth wires 52 and 53. Consequently, the head portion 310 may be tilted in the upward and downward directions.

For example, as shown in FIGS. 7 and 8, when the third wire 52 extends from first length L1 to second length L1' and the fourth wire 53 contracts from third length L2 to fourth length L2', the head portion 310 may be tilted such that the end portion of the head portion 310 may move downwardly. That is, when the third wire 52 extends and the fourth wire 53 contracts by rotation of the motor, the head portion 310 may rotate about the second joint 313 to be tilted in a direction close to the arm portion 311. In contrast, when the third wire 52 contracts and the fourth wire 53 extends, the head portion 310 may be tilted such that the end portion of the head portion 310 may move in a direction away from the arm portion 311, namely, in an upward direction. Consequently, the head portion 310 may be tilted about the second joint 313 in the upward and downward directions.

The arm portion 311 may be tilted about the third joint 314. A configuration in which the arm portion 311 is tilted about the third joint 314 is similar to a configuration in which the head portion 310 rotates about the second joint 313 in the upward and downward directions.

The other side of the third gear portion 46 may be formed with fifth teeth 462, and one side of the connection portion 20 may be formed with sixth teeth 200 corresponding to the fifth teeth 462 formed on the other side of the third gear portion 46. The third gear portion 46 and the connection portion 20 may be connected by a link (not shown), and the fifth teeth 462 of the third gear portion 46 and the sixth teeth 200 of the connection portion 20 may be configured to engage and rotate with each other. The third gear portion 46 and the connection portion 20 may be provided with a pair of wire mounting portions in the upward and downward directions, and wires connected to the motor may be respectively wound around the wire mounting portions. If one wire extends by the motor, the other wire contracts, thereby enabling the arm portion 311 to be tilted about the third joint 314 in the upward and downward directions.

Meanwhile, the third wire 52 may serve as a reducer by being wound several turns around the third wire mounting portions 48 and 48'. Similarly, the fourth wire 53 may serve as a reducer by being wound several turns around the fourth wire mounting portions 49 and 49'. For example, when the third wire 52 is wound several turns around the third wire mounting portions 48 and 48', drive force of the drive portion may be amplified and transferred to the second joint 313. In addition, drive force of the drive portion may be amplified by the fourth wire 53 which is wound several turns around the fourth wire mounting portions 49 and 49' and be transferred to the second joint 313. A reducer structure similar to a case of the second joint 313 may be applied to the third joint 314.

In some example embodiments, wires of the first joint 312 may function similar to wires of the second joint 313. In some example embodiments, wires of the third joint 314 may function similar to wires of the second joint 313.

As described above, the teeth of the gear portions engage with each other so that the gear portions rotate at the respective joints, thereby preventing the endoscopic module from sliding during rotation thereof. Accordingly, operation of the endoscopic module may be accurately controlled. The teeth formed on the outer sides of the two gear portions facing with each other at the joint engage and rotate, thereby enabling the endoscopic module to be tilted. Accordingly, since the endoscopic module may be tilted at a large angle, a viewing angle of the camera 40 may be satisfactorily secured.

Figure 10:
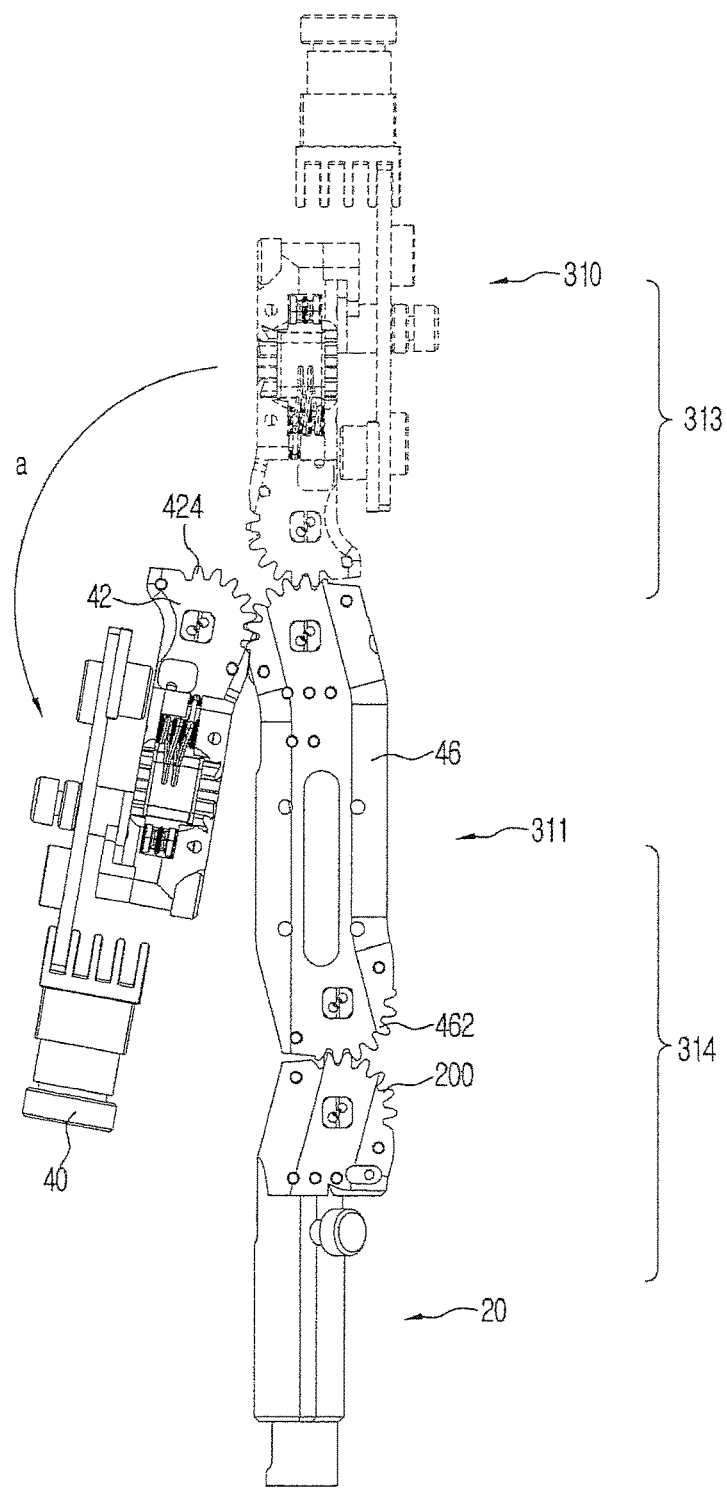

FIGS. 9 and 10 are views illustrating tilting operation of the endoscopic module according to some example embodiments.

FIG. 9 shows a tilted state of the arm portion 311 at the second and third joints 313 and 314. That is, FIG. 9 is a side view illustrating states in which the arm portion 311 of the endoscopic module 31 is tilted relative to the connection portion 20 and the head portion 310. A state in which the head portion 310 is rotated and tilted in a counterclockwise direction 'a' is shown in "A", and a state in which the head portion 310 is rotated and tilted in a clockwise direction 'b' is shown in "B". The second gear portion 42 of the head portion 310 and the third gear portion 46 of the arm portion 311 may be formed with the third teeth 424 and fourth teeth 460, respectively, so as to significantly rotate in the counterclockwise direction 'a'. As shown in "A" of FIG. 9 and FIG. 10, the head portion 310 may rotate relative to the arm portion 311 in the counterclockwise direction 'a'. For example, the head portion 310 may rotate by an angle of 170° in the counterclockwise direction 'a'. As shown in "B" of FIG. 9, the head portion 310 may also rotate relative to the arm portion 311 in the clockwise direction 'b'. For example, the head portion 310 may rotate by approximately an angle of 10° in the clockwise direction 'b'. Since the head portion 310 is configured to be slightly rotatable relative to the arm portion 311 in the clockwise direction 'b', a clear view of the camera 40 may be further enlarged.

Example embodiments are not limited to an angle by which the head portion 310 may be tilted relative to the arm portion 311. Since the endoscopic module is rotatable to a position at which the last tooth of at least one of the third teeth 424 of the second gear portion 42 and the fourth teeth 460 of the third gear portion 46 is formed, a rotation angle and a rotation direction of the endoscopic module may vary according to the forms of the teeth.

Figure 11:
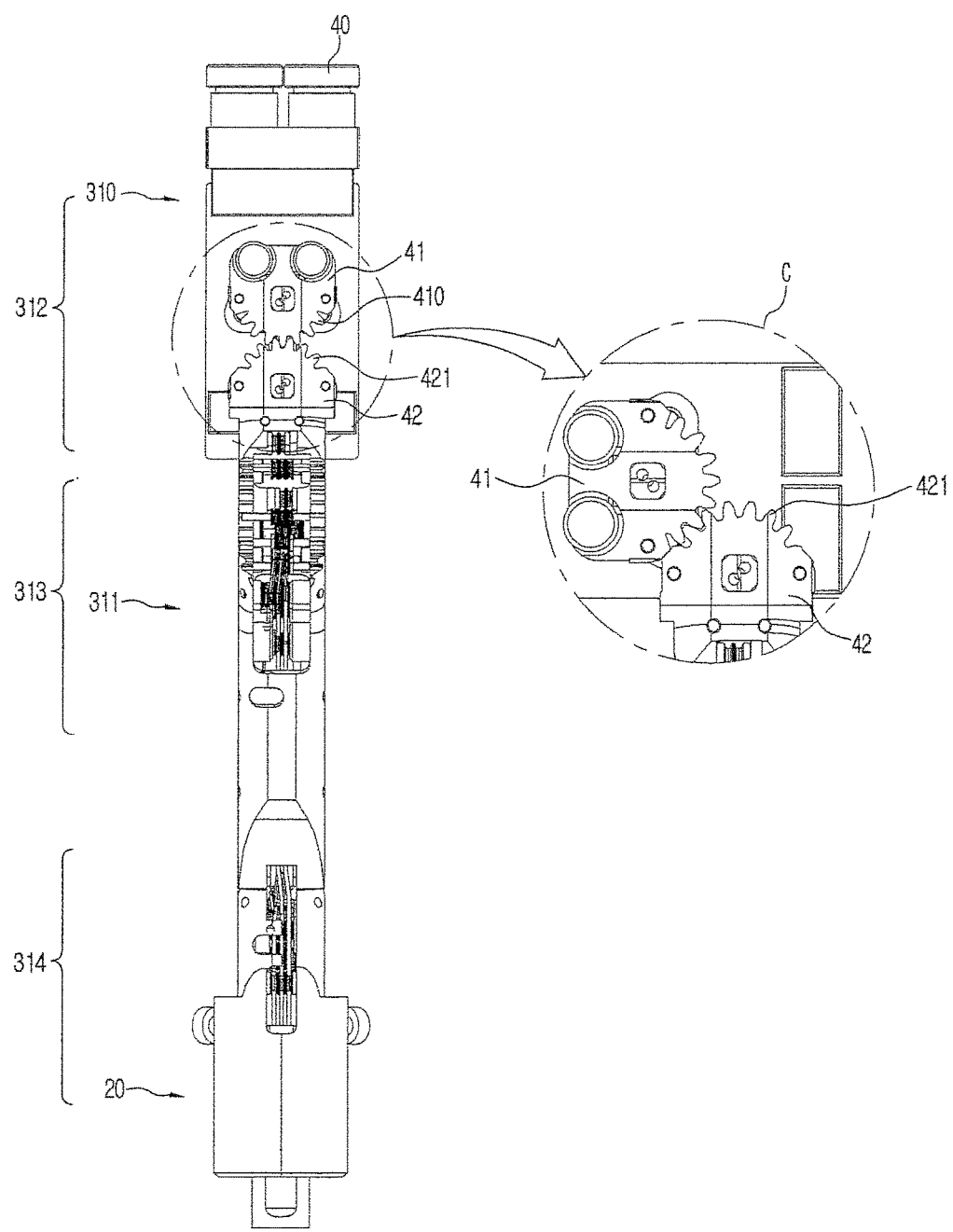
FIGS. 11 and 12 are views illustrating a rotation state of a head portion in the endoscopic module according to some example embodiments.
Figure 12:
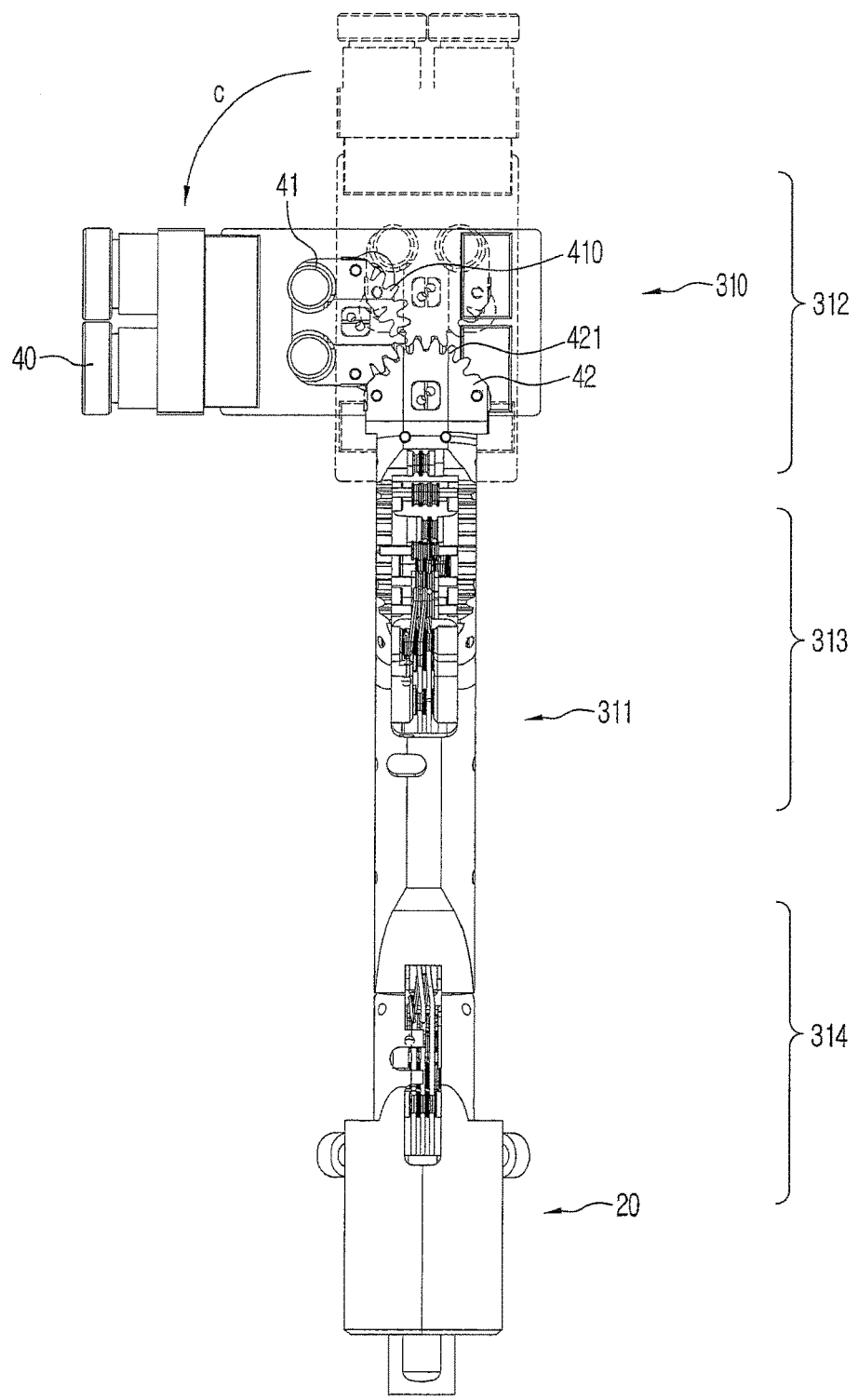

FIGS. 11 and 12 are views illustrating a rotation state of the head portion in the endoscopic module according to some example embodiments.

Referring to FIGS. 11 and 12, the head portion 310 of the endoscopic module 31 is rotatable in the left and right directions. The first teeth 410 formed on the first gear portion 41 engage with the second teeth 421 of the second gear portion 42 so that the head portion 310 is rotatable in a left direction 'c'. Similarly, the head portion 310 is rotatable in a right direction. As an example, the head portion may rotate, for example, by an angle of 90° in the left or right direction. Example embodiments are not limited to an angle by which the head portion may rotate in the left or right direction. Since the endoscopic module is rotatable to a position at which the last tooth of at least one of the first teeth 410 of the first gear portion 41 and the second teeth 421 of the second gear portion 42 is formed, a rotation angle of the endoscopic module may vary according to the forms of the teeth.

As described above, since the endoscopic module 31 is configured to form a triangular shape with the surgical instrument modules 32, imaging may be performed while the endoscopic module 31 views operation of the surgical instrument module 32. Accordingly, the camera 40 may easily capture operation of the surgical instrument module 32. Since each joint is provided in the form of a rolling joint at which the teeth of the gear portions engage and rotate with each other, a large rotation angle of the endoscopic module 31 may be formed. Since a viewing angle of the camera 40 is easily secured due to the large rotation angle of the endoscopic module 31, it may be possible to more easily capture operation of the surgical instrument module 32 at many different angles.

The endoscopic module 31 according to some example embodiments may operate with three degrees of freedom or more. That is, left and right rotation at the head portion 310, up and down tilting between the head portion 310 and the arm portion 311, and up and down tilting between the arm portion 311 and the connection portion 20 may be performed so that it may be possible to accurately capture an image for a part to be operated at several positions. Furthermore, since each joint is provided in the form of a rolling joint so as to form a large rotation angle, it may be possible to obtain images similar to those formed by zoom in/out of the camera.

As is apparent from the above description, in accordance with some example embodiments, since an image for a part to be operated at several positions is accurately provided through an endoscopic module having a plurality of joints, an operation may be properly performed in a state of accurately grasping the part to be operated. In addition, since the plural joints are provided in the forms of rolling joints so as to be capable of forming a large tilting angle of the endoscopic module, an image for a part to be operated may be more easily obtained.

While example embodiments have been particularly shown and described, it will be understood by those of ordinary skill in the art that various changes in form and details may be made therein without departing from the spirit and scope of the present invention as defined by the following claims.

What is claimed is:

1. An endoscopic surgical instrument, comprising:
   two surgical instrument modules, each of which is provided with a surgical instrument portion;
   an endoscopic module configured to form a triangular shape with the two surgical instrument modules and configured to image operations of the surgical instrument modules at different angles using a plurality of joints;
   a drive portion including a motor to generate drive forces; and
   a connection portion to connect the endoscopic module and the drive portion,
   wherein wires connecting respective members coupled by the plurality of joints are configured to amplify drive forces of the drive portion applied to the plurality of joints,
   wherein the plurality of joints comprise rolling joints at which teeth of gears engage and rotate with each other, wherein the plurality of joints provide three or more degrees of freedom to the endoscopic module, wherein the endoscopic module includes a head portion and an arm portion, wherein the head portion includes a first gear portion, a second gear portion and a camera mounted in the head portion, the first gear portion including first teeth, the second gear portion including second teeth and third teeth, the second teeth being at a first side of the second gear portion for matching with the first teeth to allow the head portion to rotate in left and right directions together with the first gear portion, and the third teeth being at a second side of the second gear portion, and the camera being mounted in the head portion to image the operations of the surgical instrument modules, wherein the arm portion is connected to the drive portion through the connection portion and connected to the head portion, the arm portion including a third gear portion, the third gear portion including fourth teeth at a first side of the third gear portion to match with the third teeth of the second gear portion to allow the head portion to rotate in upward and downward directions together with the connection portion and the second gear portion, and wherein a direction in which the second teeth extend on the first side of the second gear portion forms a right angle with a direction in which the third teeth extend on the second side of the second gear portion.

2. The endoscopic surgical instrument according to claim 1, wherein the wires include a first wire wound around left sides of the first and second gear portions and a second wire wound around right sides of the first and second gear portions:

when the first wire extends and the second wire contracts, the head portion rotates in a direction toward the right side at which the contracted second wire is located, and wherein when the first wire contracts and the second wire extends, the head portion rotates in a direction toward the left side at which the contracted first wire is located.

3. The endoscopic surgical instrument according to claim 2, wherein the first and second gear portions are provided with wire mounting portions, and wherein wires connected to the drive portion are wound around the wire mounting portions of the first and second gear portions.

4. The endoscopic surgical instrument according to claim 3, wherein the wire mounting portions of the first and second gear portions comprise:

first wire mounting portions provided at left sides of the first and second gear portions; and second wire mounting portions provided at right sides of the first and second gear portions.

5. The endoscopic surgical instrument according to claim 4, wherein the first wire is wound around the first wire mounting portions, the second wire is wound around the second wire mounting portions, and when one of the first and second wires is contracted by the drive portion and the other one of the first and second wires extends, the head portion is configured to rotate toward the contracted one of the first and second wires.

6. The endoscopic surgical instrument according to claim 1, wherein when the head portion is tilted in upward and downward directions, the third teeth and the fourth teeth engage and rotate with each other.

7. The endoscopic surgical instrument according to claim 6, wherein the second side of the second gear portion and the first side of the third gear portion are provided with wire mounting portions, and wires connected to the drive portion are wound around the wire mounting portions of the second side of the second gear portion and the first side of the third gear portion.

8. The endoscopic surgical instrument according to claim 7, wherein the wire mounting portions of the second side of the second gear portion and the first side of the third gear portion comprise:

third wire mounting portions respectively provided at upper portions of the second and third gear portions; and fourth wire mounting portions respectively provided at lower portions of the second and third gear portions.

9. The endoscopic surgical instrument according to claim 8, wherein a third wire is wound around the third wire mounting portions, a fourth wire is wound around the fourth wire mounting portions, and when one of the third and fourth wires is contracted by the drive portion and the other one of the third and fourth wires extends, the head portion is configured to rotate and tilt toward the contracted one of the third and fourth wires.

10. The endoscopic surgical instrument according to claim 1, wherein a second side of the third gear portion includes fifth teeth, the connection portion includes sixth teeth corresponding to the fifth teeth, and when the arm portion is tilted in upward and downward directions, the fifth teeth and the sixth teeth engage and rotate with each other.

11. The endoscopic surgical instrument according to claim 10, wherein an upper side of the third gear portion and a lower side of the connection portion are respectively provided with wire mounting portions, fifth and sixth wires connected to the drive portion are wound around the respective wire mounting portions of the upper side of the third gear portion and the lower side of the connection portion, and when one of the fifth and sixth wires is contracted by the drive portion and the other one of the fifth and sixth wires extends, the arm portion is configured to rotate and tilt toward the contracted one of the fifth and sixth wires.

12. The endoscopic surgical instrument according to claim 10, wherein a tilting direction or a tilting angle of the head portion or the arm portion is configured to vary according to a direction or a length in which the second teeth, the third teeth, the fourth teeth, the fifth teeth, or the sixth teeth extend.

* * * * *